(12) United States Patent
Chaki et al.

(10) Patent No.: US 10,590,051 B2
(45) Date of Patent: Mar. 17, 2020

(54) METHOD FOR PRODUCING FLUORINE-CONTAINING OLEFIN

(71) Applicant: DAIKIN INDUSTRIES, LTD., Osaka (JP)

(72) Inventors: Takehiro Chaki, Osaka (JP); Shun Ohkubo, Osaka (JP); Daisuke Karube, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days.

(21) Appl. No.: 15/576,430

(22) PCT Filed: May 18, 2016

(86) PCT No.: PCT/JP2016/064781
§ 371 (c)(1),
(2) Date: Nov. 22, 2017

(87) PCT Pub. No.: WO2016/194616
PCT Pub. Date: Dec. 8, 2016

(65) Prior Publication Data
US 2018/0155260 A1    Jun. 7, 2018

(30) Foreign Application Priority Data

May 29, 2015 (JP) .................... 2015-110774

(51) Int. Cl.
*B01D 3/14* (2006.01)
*B01D 3/40* (2006.01)
(Continued)

(52) U.S. Cl.
CPC .............. *C07C 17/25* (2013.01); *B01J 23/26* (2013.01); *C07C 21/18* (2013.01); *C08F 14/18* (2013.01);
(Continued)

(58) Field of Classification Search
CPC ...... C07C 17/25; C07C 17/358; C07C 17/383; C07C 21/18; C07C 19/08; B01J 23/26;
(Continued)

(56) References Cited

U.S. PATENT DOCUMENTS

2010/0305370 A1    12/2010   Devic et al.
2011/0152585 A1*   6/2011    Takahashi .............. C07C 17/25
                                                570/151
(Continued)

FOREIGN PATENT DOCUMENTS

JP    2009-513719    4/2009
JP    2009-542651    12/2009
(Continued)

OTHER PUBLICATIONS

International Search Report dated Jul. 5, 2016 in International (PCT) Application No. PCT/JP2016/064781.
(Continued)

*Primary Examiner* — Jafar F Parsa
(74) *Attorney, Agent, or Firm* — Wenderoth, Lind & Ponack, L.L.P.

(57) ABSTRACT

The present invention provides a method for producing a target fluorine-containing olefin with high conversion and selectivity using a process comprising a dehydrofluorination reaction of a hydrofluorocarbon. The method comprises a first reaction step comprising subjecting a hydrofluorocarbon to dehydrofluorination in the presence of a catalyst. The hydrofluorocarbon is a compound represented by Formula (1): $R^fCFYCHZ_2$, wherein $R^f$ represents a straight or branched $C_{1-3}$ perfluoroalkyl group, and Y and Z each independently represent H or F wherein when all Zs are H, Y represents F. The catalyst comprises chromium oxide represented by the chemical formula: $CrO_m$ ($1.5<m<3$).

10 Claims, 1 Drawing Sheet

(51) Int. Cl.
*B01J 23/26* (2006.01)
*C07B 61/00* (2006.01)
*C07C 17/25* (2006.01)
*C07C 21/18* (2006.01)
*C08F 14/18* (2006.01)

(52) U.S. Cl.
CPC ............ *B01D 3/14* (2013.01); *B01D 3/40* (2013.01); *C07B 61/00* (2013.01)

(58) Field of Classification Search
CPC . B01J 2523/55; B01J 2523/56; B01J 2523/57
See application file for complete search history.

(56) References Cited

U.S. PATENT DOCUMENTS

| | | | | |
|---|---|---|---|---|
| 2012/0302802 | A1* | 11/2012 | Komatsu | C07C 17/25 570/156 |
| 2014/0303412 | A1* | 10/2014 | Karube | C07C 17/206 570/160 |

FOREIGN PATENT DOCUMENTS

| | | |
|---|---|---|
| JP | 2010-531897 | 9/2010 |
| JP | 2011-515457 | 5/2011 |
| JP | 2011-520016 | 7/2011 |
| JP | 2012-500182 | 1/2012 |
| JP | 2012-77086 | 4/2012 |
| JP | 2012-528878 | 11/2012 |
| JP | 2013-519628 | 5/2013 |
| JP | 2015-509096 | 3/2015 |
| WO | 2007/053736 | 5/2007 |
| WO | 2008/002500 | 1/2008 |
| WO | 2009/003157 | 12/2008 |
| WO | 2009/084703 | 7/2009 |
| WO | 2009/137656 | 11/2009 |
| WO | 2010/021406 | 2/2010 |
| WO | 2010/141664 | 12/2010 |
| WO | 2011/099604 | 8/2011 |
| WO | 2013/111911 | 8/2013 |

OTHER PUBLICATIONS

Extended European Search Report dated Jan. 8, 2019 in corresponding European Application No. 16803051.8.

* cited by examiner

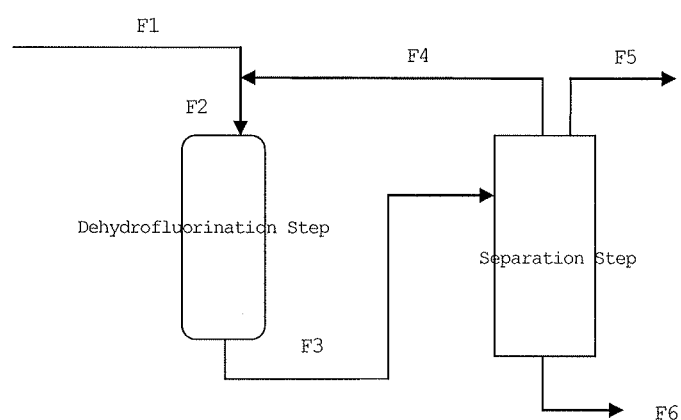

METHOD FOR PRODUCING FLUORINE-CONTAINING OLEFIN

TECHNICAL FIELD

The present invention relates to a method for producing a fluorine-containing olefin.

BACKGROUND ART

Fluoroolefins represented by the formula: $CF_3(CX_2)_nCF=CH_2$, the formula: $CF_3(CX_2)_nCH=CHF$ (wherein X represents halogen), and the like are useful compounds as, for example, various functional materials, solvents, refrigerants, blowing agents, and monomers for functional polymers or starting materials of such monomers. In particular, of the fluoroolefins mentioned above, 2,3,3,3-tetrafluoropropene (hereinafter abbreviated as "HFO-1234yf") represented by $CF_3CF=CH_2$ has gained attention because it offers promising prospects as a refrigerant compound of low global-warming potential.

The HFO-1234yf is known to be produced by a method comprising fluorinating a halopropane or halopropene used as a starting material by using hydrogen fluoride (HF), or by a method suitably combining hydrogenation and dehydrohalogenation. For example, as also disclosed in Patent Literature (PTL) 1, when 1,1,1,2,3,3-hexafluoropropene (HFO-1216) is used as a starting material, the HFO-1234yf is produced in accordance with the following reaction process:

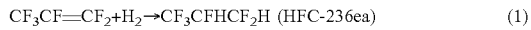

$$CF_3CF=CF_2 + H_2 \rightarrow CF_3CFHCF_2H \text{ (HFC-236ea)} \quad (1)$$

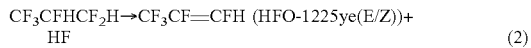

$$CF_3CFHCF_2H \rightarrow CF_3CF=CFH \text{ (HFO-1225ye(E/Z))} + HF \quad (2)$$

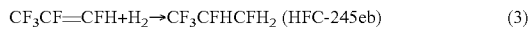

$$CF_3CF=CFH + H_2 \rightarrow CF_3CFHCFH_2 \text{ (HFC-245eb)} \quad (3)$$

$$CF_3CFHCFH_2 \rightarrow CF_3CF=CH_2 \text{ (HFO-1234yf)} + HF \quad (4)$$

A reaction process is also known that comprises fluorinating HFO-1243zf to obtain HFC-245eb as in reaction formula (5) below, and conducting a reaction represented by reaction formula (4) above to obtain HFO-1234yf.

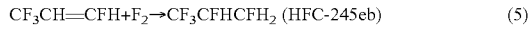

$$CF_3CH=CFH + F_2 \rightarrow CF_3CFHCFH_2 \text{ (HFC-245eb)} \quad (5)$$

$$CF_3CFHCFH_2 \rightarrow CF_3CF=CH_2 \text{ (HFO-1234yf)} + HF \quad (4)$$

Accordingly, in any reaction process, HFC-245eb is subjected to a dehydrofluorination reaction to produce HFO-1234yf. The dehydrofluorination reaction has been considered in various ways (see, for example, PTL 2 to PTL 4), and methods have been proposed for efficiently producing a fluorine-containing olefin, such as HFO-1234yf, by suitably adjusting the type of catalyst, reaction temperature, contact time, and the like.

CITATION LIST

Patent Literature

PTL 1: J2012-77086A
PTL 2: JP2009-542651A
PTL 3: JP2011-515457A
PTL 4: JP2009-513719A

SUMMARY OF INVENTION

Technical Problem

However, a dehydrofluorination reaction of a hydrofluorocarbon, such as 245eb, requires some large amount of catalyst, as well as a relatively high reaction temperature. Therefore, in known methods, $CF_3CH=CHF$ (HFO-1234ze), i.e., isomers of the target product, would be problematically easily produced in a large amount as by-products, in addition to the target product. A decrease in the lifetime of catalyst used in the reaction is also a problem to be solved. The problem regarding a decrease in the lifetime of catalyst could be solved by using oxygen in combination. In this case, however, the yield would problematically decrease since combustion of the starting material and the target product would be accelerated.

The present invention has been made in view of such problems, and an object of the present invention is to provide a method for producing a target fluorine-containing olefin with a high selectivity using a process comprising subjecting a hydrofluorocarbon to a dehydrofluorination reaction.

Solution to Problem

In order to achieve the above object, the present inventors conducted extensive research, and found that the above object is achieved by using $CrO_m$ (1.5<m<3) as a catalyst in a dehydrofluorination reaction of a hydrofluorocarbon to produce a fluorine-containing olefin. The present invention has thus been accomplished.

More specifically, the present invention relates to the following method for producing a fluorine-containing olefin.
Item 1. A method for producing a fluorine-containing olefin, the method comprising a first reaction step comprising subjecting a hydrofluorocarbon to dehydrofluorination in the presence of a catalyst,
the hydrofluorocarbon being a compound represented by Formula (1): $R^fCFYCHZ_2$, wherein $R^f$ represents a straight or branched $C_{1-3}$ perfluoroalkyl group, and Y and Z each independently represent H or F, wherein when all Zs are H, Y represents F, the catalyst comprising chromium oxide represented by the chemical formula: $CrO_m$, wherein 1.5<m<3.
Item 2. The method for producing a fluorine-containing olefin according to Item 1, wherein the catalyst is chromium oxide represented by the chemical formula: $CrO_m$, wherein 2.0≤m<3.
Item 3. The method for producing a fluorine-containing olefin according to Item 1, wherein the catalyst is chromium oxide represented by the chemical formula: $CrO_m$, wherein 2.05≤m≤2.3.
Item 4. The method for producing a fluorine-containing olefin according to any one of Items 1 to 3, wherein $R^f$ in Formula (1) represents $CF_3$.
Item 5. The method for producing a fluorine-containing olefin according to Item 4, wherein the hydrofluorocarbon comprises at least one member selected from the group consisting of HFC-236ea, HFC-245eb, and HFC-245cb.
Item 6. The method for producing a fluorine-containing olefin according to Item 5, wherein the hydrofluorocarbon is HFC-245eb.
Item 7. The method for producing a fluorine-containing olefin according to any one of Items 1 to 6, wherein the hydrofluorocarbon is HFC-245eb, and wherein a total S1 (mol/min) is 20% or less, relative to a flow rate S (mol/min), the flow rate S being a flow rate of an entire reaction product discharged after the first reaction step from a reactor in which the first reaction step is performed, the total S1 being a flow rate of E- and Z-isomers of HFO-1234ze and a flow rate of HFC-245fa contained in the entire reaction product.

Item 8. The method for producing a fluorine-containing olefin according to Item 7, wherein the total S1 (mol/min) is 10% or less, relative to the flow rate S (mol/min).

Item 9. The method for producing a fluorine-containing olefin according to Item 7, wherein the total S1 (mol/min) is 5% or less, relative to the flow rate S (mol/min).

Item 10. The method for producing a fluorine-containing olefin according to any one of Items 1 to 9, wherein the dehydrofluorination in the first reaction step is performed at 50 to 400° C.

Item 11. The method for producing a fluorine-containing olefin according to any one of Items 1 to 9, wherein the dehydrofluorination in the first reaction step is performed at 100 to 400° C.

Item 12. The method for producing a fluorine-containing olefin according to any one of Items 1 to 9, wherein the dehydrofluorination in the first reaction step is performed at 230 to 400° C.

Item 13. The method for producing a fluorine-containing olefin according to any one of Items 5 to 12, the method comprising a separation step after the first reaction step, the separation step comprising separating a portion of or all of the outflow obtained from the reactor in which the first reaction step is performed into at least a first fraction and a second fraction, wherein the first fraction has a greater concentration of HFC-245eb than before the separation step, and the second fraction has a lower concentration of HFC-245eb than before the separation step, and
wherein at least a portion of the first fraction is subjected to dehydrofluorination after the separation step.

Item 14. The method for producing a fluorine-containing olefin according to any one of Items 5 to 12, the method comprising a separation step after the first reaction step, the separation step comprising separating a portion of or all of the outflow obtained from the reactor in which the first reaction step is performed into at least a third fraction and a fourth fraction, wherein the third fraction has a greater concentration of HFC-245cb than before the separation step, and the fourth fraction has a lower concentration of HFC-245cb than before the separation step, and
wherein at least a portion of the third fraction is subjected to dehydrofluorination after the separation step.

Item 15. The method for producing a fluorine-containing olefin according to Item 13, wherein at least a portion of the first fraction is reused in the first reaction step of dehydrofluorination.

Item 16. The method for producing a fluorine-containing olefin according to Item 14, wherein at least a portion of the third fraction is reused in the first reaction step of dehydrofluorination.

Item 17. The method for producing a fluorine-containing olefin according to any one of Items 1 to 16, wherein the hydrofluorocarbon is subjected in combination with oxygen gas to the first reaction step.

Item 18. The method according to Item 17, wherein a flow rate (mol/min) of the oxygen gas is 0.1% or more and 10% or less, relative to a flow rate (mol/min) of the hydrofluorocarbon.

Item 19. The method for producing a fluorine-containing olefin according to any one of Items 1 to 18, wherein the chromium oxide further contains a Group 5 metal.

Item 20. The method for producing a fluorine-containing olefin according to Item 19, wherein the number of atoms of the Group 5 metal contained in the chromium oxide is 0.1% or more and 50% or less, relative to the total number of atoms of the metal contained in the chromium oxide.

Advantageous Effects of Invention

In the method for producing a fluorine-containing olefin according to the present invention, chromium oxide represented by the chemical formula: $CrO_m$ (wherein m is $1.5<m<3$) is used as a catalyst to perform a dehydrofluorination reaction of a specific hydrofluorocarbon. This makes it possible to obtain a target product with a high selectivity. Even when a dehydrofluorination reaction is performed at a low temperature, a target product is obtained with a high selectivity.

BRIEF DESCRIPTION OF DRAWINGS

FIG. 1 is a schematic diagram showing the flow of the production of Example 4-1.

DESCRIPTION OF EMBODIMENTS

The following are specific embodiments according to the present invention.

The method for producing a fluorine-containing olefin according to this embodiment comprises a first reaction step, in which a hydrofluorocarbon is subjected to dehydrofluorination in the presence of a catalyst to produce a fluorine-containing olefin. In particular, in this embodiment, the catalyst comprises chromium oxide represented by the chemical formula: $CrO_m$ ($1.5<m<3$). The method for producing a fluorine-containing olefin according to this embodiment, which uses the catalyst described above, is capable of producing a target product with a high selectivity. Even when the dehydrofluorination reaction is performed at a low temperature, the target product is obtained with a high selectivity.

In the first reaction step, a hydrofluorocarbon is subjected to dehydrofluorination in the presence of the catalyst.

The hydrofluorocarbon above is a compound represented by Formula (1): $R^fCFYCHZ_2$. In Formula (1), $R^f$ represents a straight or branched $C_{1-3}$ perfluoroalkyl group, and Y and Z each independently represent H or F, wherein when all Zs are H, Y represents F.

$R^f$ is not particularly limited as long as it represents a straight or branched $C_{1-3}$ perfluoroalkyl group. $R^f$ is preferably $CF_3$ (trifluoromethyl). In this case, a fluorine-containing olefin is produced with higher conversion and selectivity.

The hydrofluorocarbon may consist of, but is not limited to, only a single compound represented by Formula (1). It is also possible that the hydrofluorocarbon comprises two or more compounds represented by Formula (1).

The hydrofluorocarbon preferably comprises at least one member selected from the group consisting of HFC-236ea, HFC-245eb, and HFC-245cb. In this case, a fluorine-containing olefin is produced with higher conversion and selectivity.

HFC-236ea refers to 1,1,1,2,3,3-hexafluoropropane, HFC-245eb refers to 1,1,1,2,3-pentafluoropropane, and HFC-245cb refers to 1,1,1,2,2-pentafluoropropane.

The hydrofluorocarbon may be, but is not limited to, a commercially available product or that produced, for example, by hydrogen reduction of a double bond-containing hydrofluorocarbon. For example, hydrogen reduction of a hexafluoropropane yields HFC-236ea, while hydrogen reduction of 1,2,3,3,3-pentafluoropropene (HFO-1225ye) yields HFC-245eb.

In the production method according to this embodiment, a catalyst comprises chromium oxide represented by the chemical formula: $CrO_m$ (1.5<m<3), as described above.

The chromium oxide represented by the $CrO_m$ is such that m is within the range of 1.5<m<3, and that the chromium in the chromium oxide has a valence exceeding 3.

In the $CrO_m$ representing chromium oxide, m is preferably $1.75 \leq m \leq 2.5$, also preferably $2 \leq m < 3$, more preferably $2 \leq m \leq 2.4$, and particularly preferably $2.05 \leq m \leq 2.3$. In this case, a fluorine-containing olefin is produced with a higher selectivity, and the conversion of hydrofluorocarbon used as the starting material also improves. The valence of chromium can be measured by a known method.

The following is an example of the preparation method of chromium oxide.

First, an aqueous solution of chromium salt is mixed with aqueous ammonia to obtain precipitates of chromium hydroxide. Examples of the chromium salt include chromium nitrate, chromium chloride, chromium alum, chromium sulfate, and the like. For example, about 1 equivalent or more of aqueous ammonia per equivalent of chromium nitrate is added dropwise to an aqueous chromium nitrate solution to obtain precipitates of chromium hydroxide.

The precipitates are then filtered and washed, followed by drying. The drying is performed, for example, in the air at about 70 to 200° C., in particular, about 120° C., for about 1 to 100 hours, in particular, about 12 hours. The reaction product at this stage is referred to as being in a state of chromium hydroxide. This reaction product is then crushed.

The powder of the chromium hydroxide obtained by crushing is formed into pellets with a tableting machine. The size of the pellets may be, for example, about 3.0 mm in diameter and about 3.0 mm in height.

It is preferable that the formed pellets are calcined in an inert atmosphere, for example, in a nitrogen stream, to produce an amorphous chromium oxide.

In this manner, chromium oxide that is used in the production method according to this embodiment is prepared.

The chromium oxide may further contain a Group 5 metal. In this case, a fluorine-containing olefin is produced with a higher selectivity, and the conversion of hydrofluorocarbon used as the starting material also improves.

The state of the Group 5 element is not particularly limited as long as the Group 5 element is present simultaneously with the chromium oxide. For example, the Group 5 element may be unevenly distributed on the surface of the chromium oxide, or the Group 5 element may be uniformly mixed with the chromium oxide. In these cases, the Group 5 element may be present as a metal or in the state of oxide, oxy fluoride, or the like, and is preferably present in the state of oxide or oxy fluoride. Further, the Group 5 element may be partially or wholly combined with a chromium metal to form a complex oxide. The chromium oxide containing a Group 5 element may be in a crystalline state or an amorphous state. A mixture of chromium oxide in a crystalline state and chromium oxide in an amorphous state may also be used.

Examples of the Group 5 element include vanadium, niobium, tantalum, and the like. Vanadium, niobium, and the like are preferable because they are easily available and exhibit high performance. In particular, niobium is preferable. The Group 5 elements may be contained singly, or in a combination of two or more.

The Group 5 element is preferably present in a quadrivalent or pentavalent state. In this case, a compound containing a zerovalent to trivalent Group 5 element may be used as a starting material to produce a catalyst, and may be oxidized to a quadrivalent to pentavalent state during the process of producing a catalyst.

The amount of the Group 5 element is not particularly limited. From the viewpoint of suppressing a decrease in selectivity, the number of atoms of the Group 5 metal contained in the chromium oxide is preferably 0.1% or more and 50% or less, and more preferably 0.5% or more and 15% or less, relative to the total number of atoms of the metal contained in the chromium oxide. Further, when the Group 5 element is vanadium, the number of atoms of vanadium contained in chromium oxide is preferably 0.1% or more and 50% or less, more preferably 0.5% or more and 15% or less, and particularly preferably 0.5% or more and 3% or less, relative to the total number of atoms of the entire metal contained in the chromium oxide.

The method for producing chromium oxide containing a Group 5 metal is not particularly limited. Examples of the method for producing chromium oxide containing a Group 5 element include the following: a method comprising adding chromium oxide or chromium hydroxide, i.e., a precursor of chromium oxide, to a solution containing a Group 5 element to achieve impregnation of the Group 5 element, removing the solvent, and calcinating the residue (impregnation method); a method comprising precipitating Cr and a Group 5 element as hydroxide, ammonium salt, carbonate, hydrogencarbonate, etc., from a solution containing the Cr and the Group 5 element, followed by washing, drying, and calcinating the precipitates (coprecipitation method); a method comprising subjecting a solution containing Cr and a Group 5 element to a hydrothermal synthesis reaction to precipitate the Cr and the Group 5 element from the solution, followed by calcination of the separated precipitates (hydrothermal synthesis method); a method comprising physically mixing salts containing Cr and a Group 5 element, oxides containing Cr and a Group 5 element, or the like using a mortar or the like, and optionally calcinating the mixture (kneading method); and the like. Examples also include a method comprising physically mixing a sublimable metal salt containing a Group 5 element, such as niobium chloride, vanadium chloride, or tantalum chloride, with chromium oxide using a mortar or the like; heating the resulting mixture to the sublimation temperature of the sublimable metal salt to deposit the sublimed metal salt on the chromium oxide; and optionally decomposing the sublimable metal salt so that the metal or metal oxide is supported on the chromium oxide (chemical vapor deposition method; CVD method) (see JP2015-509096A).

The chromium oxide used as a catalyst may be a so-called fluorinated chromium oxide obtained by fluorination. This fluorination may be performed in accordance with a known method.

A catalyst supported on a carrier, such as alumina, aluminum fluoride, fluorinated aluminum oxide, or active carbon, may also be used.

As a catalyst, the chromium oxide above may be used singly or in a combination with other catalysts, as long as the effect of the present invention is achieved. For use as a catalyst, the chromium oxide containing a Group 5 element may further contain a component other than the Group 5 metal. Specific examples of the component other than the Group 5 metal include metals, such as indium, gallium, nickel, copper, and zinc; fluorides of these metals; oxides of these metals; oxy fluorides of these metals; and the like. Examples of the component other than the Group 5 metal also include non-metals, such as carbon.

When the component other than the Group 5 metal is present together with chromium oxide, the chromium content may be 30% or more, preferably 50% or more, and more preferably 90% or more, relative to the total number of atoms contained in the chromium oxide.

The following describes the reaction conditions of the first reaction step other than the above.

In the dehydrofluorination reaction of a hydrofluorocarbon in the first reaction step, the reaction pressure is not particularly limited, and the reaction may proceed under reduced pressure, ordinary pressure, or increased pressure. In particular, a reaction under ordinary pressure is advantageous from the viewpoint of equilibrium, compared with a reaction under increased pressure, and is also advantageous because it does not require a relatively large device, unlike a reaction under reduced pressure.

The reactor used in the first reaction step may be, but is not particularly limited to, a reactor formed of a material, such as Hastelloy, Inconel, or Monel.

The upper limit of the reaction temperature of dehydrofluorination in the first reaction step, when under ordinary pressure, is preferably 400° C., more preferably 380° C., still more preferably 350° C., particularly preferably 330° C., and most particularly preferably 300° C., from the viewpoint of reducing energy waste, suppressing selectivity reduction, and suppressing catalyst deterioration. The lower limit of the reaction temperature of dehydrofluorination in the first reaction step, when under ordinary pressure, is preferably 50° C., more preferably 100° C., still more preferably 200° C., particularly preferably 230° C., and most particularly preferably 270° C., to make it easy to prevent the conversion from unacceptably reducing, in view of the productivity.

In general, a dehydrofluorination reaction of a hydrofluorocarbon must be performed at a relatively high temperature. However, the production method according to this embodiment, which is performed using the specific catalyst having high activity, makes it possible to perform the reaction at a temperature lower than conventional temperatures. When the reaction is performed at a low temperature, it is possible to further reduce by-products that are produced in the reaction at a high temperature, and also easily suppress a decrease in the lifetime of catalyst.

The contact time in the first reaction step is not particularly limited, and may be, for example, 0.1 to 300 seconds. The value of W/F0 (g·sec·ml$^{-1}$) is also not particularly limited, and may be, for example, 0.1 to 350. The F0 (Nml·sec$^{-1}$) refers to an amount of starting material-containing gas supplied to a reactor, and the W (g) refers to an amount of catalyst placed in the reactor.

In the first reaction step, the method for supplying a hydrofluorocarbon to a reactor is not limited. For example, a hydrofluorocarbon may be supplied together with oxygen gas to be used in the first reaction step. In this case, the flow rate (mol/min) of oxygen gas may be, for example, 0.1% or more and 30% or less, preferably 0.5% or more and 15% or less, and more preferably 1% or more and 10% or less, relative to the flow rate (mol/min) of hydrofluorocarbon. This makes it easy to suppress a reduction in catalytic activity, and makes it possible to obtain a target fluorine-containing olefin continuously for a long period of time with a high selectivity. The flow rate (mol/min) of oxygen gas may also be 0.1% or more and 10% or less, relative to the flow rate (mol/min) of hydrofluorocarbon.

When a hydrofluorocarbon is supplied to a reactor, a gas such as nitrogen, helium, and argon, which are inert to the starting material or catalyst, may also be supplied together. However, when an inert gas is mixed with the starting material, a target product and the inert gas must be separated and recovered by rectification or extractive distillation. In this case, since N$_2$, which is an inert gas, is a non-condensable gas, N$_2$ is recovered together with an organic component comprising the target product. This may possibly reduce the recovery rate of the target product. From this viewpoint, when a hydrofluorocarbon is supplied to a reactor, the amount of inert gas is preferably less than 50 mol %, more preferably less than 10 mol %, and particularly preferably less than 2 mol %, relative to the total amount of the hydrofluorocarbon and inert gas; most preferably, an inert gas is not used together with the hydrofluorocarbon.

The dehydrofluorination reaction in the first reaction step may be performed by, for example, continuously supplying the starting material from the inlet of a reactor to allow the reaction to proceed in the reactor, and then continuously discharging the reaction product from the outlet of the reactor (i.e., continuous reaction system).

Although it depends on the reaction temperature, the dehydrofluorination reaction may be performed in either a gas phase or a liquid phase. To obtain the target fluorine-containing olefin with a high selectivity, the reaction is preferably performed in a gas phase.

After the first reaction step above, the target fluorine-containing olefin is produced.

The fluorine-containing olefin is represented by Formula (2): R$^f$CF=CHZ, wherein R$^f$ and Z are as defined in Formula (1).

Specific fluorine-containing olefins vary depending on the type of a hydrofluorocarbon used as the starting material. For example, when HFC-245eb or HFC-245cb is used as the hydrofluorocarbon, the resulting fluorine-containing olefin is 1,1,1,2-tetrafluoropropene (HFO-1234yf). When HFC-236ea is used as the hydrofluorocarbon, the resulting fluorine-containing olefin is 1,2,3,3,3-pentafluoropropene (HFO-1225ye). Similarly, when 1,1,2,2,3-pentafluoropropane (HFC-245ca) is used as the hydrofluorocarbon, the resulting fluorine-containing olefin is 1,1,2,3-pentafluoropropene (HFO-1234ye).

The reaction product obtained from dehydrofluorination in the first reaction step may be, for example, discharged and extracted from the outlet of the reactor.

The production method according to this embodiment achieves high conversion of a hydrofluorocarbon used as the starting material after a dehydrofluorination reaction, as well as a high selectivity of the target fluorine-containing olefin. Therefore, for example, a large amount of the target fluorine-containing olefin is contained in the flow rate S (mol/min) of the total reaction product discharged after the first reaction step from the reactor in which the first reaction step is performed. That is, a small amount of by-products is contained in the flow rate S (mol/min) of the total reaction product. Specific examples are shown below for a detailed explanation.

For example, when the hydrofluorocarbon is HFC-245eb, HFO-1234yf is obtained as the target fluorine-containing olefin; however, the E-isomer of 1,3,3,3-tetrafluoropropene (hereinafter abbreviated as HFO-1234ze), the Z-isomer of HFO-1234ze, and 1,1,1,3,3-pentafluoropropane (hereinafter abbreviated as HFC-245fa) are usually produced as by-products, and additionally, HFC-245cb and $CO_2$ may also sometimes be produced as by-products. In particular, it is preferable that the E- and Z-isomers of HFO-1234ze and HFC-245fa, which possibly deteriorate the performance of the target product, be produced in amounts as small as possible.

In this regard, in the production method according to this embodiment, the E- and Z-isomers of HFO-1234ze and HFC-245fa are produced in reduced amounts. More specifically, the total S1 (mol/min) can be 20% or less, relative to the flow rate S (mol/min). Here, the flow rate S (mol/min) refers to the flow rate of the total reaction product discharged after the first reaction step from the reactor in which the first reaction step is performed, and the total S1 (mol/min) refers to the flow rate of the E- and Z-isomers of HFO-1234ze and the flow rate of HFC-245fa contained in the total reaction product. Specifically, the proportion of the by-products can be low in the total reaction product, whereas the proportion of HFO-1234yf, which is the target product, can be high. The total S1 (mol/min) is more preferably 10% or less, and particularly preferably 5% or less, relative to the flow rate S (mol/min) of the total reaction product.

As described above, the target product is obtained with a high selectivity in the production method according to this embodiment; thus, the fluorine-containing olefin, which is the target product, is produced with high purity. For this reason, the outflow discharged after the first reaction step from the reactor can be used directly as a fluorine-containing olefin without purification.

It is also possible to perform purification of the thus obtained outflow to obtain a higher purity fluorine-containing olefin. When purification is performed, a fraction comprising an unreacted hydrofluorocarbon, by-products, and the like is obtained, the fraction of which can be reused. More specifically, in the production method according to this embodiment, a separation step may be conducted after the first reaction step. In the separation step, a portion of or all of the outflow from the reactor in which the first reaction step is performed is separated into at least two or more fractions. Specific examples are shown below for a detailed explanation.

For example, when the hydrofluorocarbon is at least one member selected from the group consisting of HFC-236ea, HFC-245eb, and HFC-245cb, the above outflow obtained in the first reaction step from the reactor in which the first reaction step is performed can contain HFC-245eb, in addition to HFO-1234yf, which is the target product, and the by-products stated above. This HFC-245eb is an unreacted material when the hydrofluorocarbon used as the starting material comprises HFC-245eb, and is a by-product when the starting material is HFC-236ea or HFC-245cb, rather than HFC-245eb.

In either case, a portion of or all of the outflow from the reactor in which the first reaction step is performed may be separated into a first fraction and a second fraction in the separation step. The means for separation is not particularly limited. For example, the separation may be performed by a distillation operation utilizing a difference in boiling point. When this separation step is performed, it is possible to obtain, for example, a fraction having a greater concentration of HFC-245eb than before the separation step (a first fraction), and a fraction having a lower concentration of HFC-245eb than before the separation step (a second fraction).

After the separation step, when a portion of or all of the first fraction is subjected to a dehydrofluorination reaction, HFC-245eb in the first fraction is dehydrofluorinated to yield HFO-1234yf. In this manner, it is possible to effectively use a hydrofluorocarbon (HFC-245eb), which is a starting material, to efficiently produce HFO-1234yf.

The dehydrofluorination of HFC-245eb contained in the first fraction may be performed in the first reaction step. Specifically, the outflow obtained in the first reaction step is separated into a first fraction and a second fraction in the separation step, and the obtained first fraction may be reused again in the first reaction step. In this case, HFO-1234yf is more efficiently produced, and the conversion of the starting material and the selectivity of the target product are further improved.

As a matter of course, the dehydrofluorination of HFC-245eb contained in the first fraction may be performed in a reaction step (e.g., a second reaction step) separately from the first reaction step. In this second reaction step as well, a dehydrofluorination reaction may be performed under the same conditions as in the first reaction step.

Further, for example, when the hydrofluorocarbon is at least one member selected from the group consisting of HFC-236ea, HFC-245eb, and HFC-245cb, the outflow obtained after the first reaction step from the reactor in which the first reaction step is performed can contain unreacted HFC-245cb, in addition to HFO-1234yf, which is the target product. This HFC-245cb is an unreacted material when the hydrofluorocarbon comprises HFC-245cb, and is a by-product when the starting material is HFC-236ea or HFC-245eb, rather than HFC-245cb.

In this case as well, when the separation step is conducted as described above, a portion of or all of the outflow from the reactor in which the first reaction step is performed may be separated into two types of fractions (a third fraction and a fourth fraction). For example, the third fraction has a greater concentration of HFC-245cb than before the separation step, while the fourth fraction has a lower concentration of HFC-245cb than before the separation step.

Then, after the separation step, when at least a portion of the third fraction is subjected to dehydrofluorination, HFC-245cb in the third fraction is dehydrofluorinated to yield HFO-1234yf. In this manner, it is possible to effectively use a hydrofluorocarbon (HFC-245cb), which is a starting material, to efficiently produce HFO-1234yf.

The dehydrofluorination of HFC-245cb contained in the third fraction may be performed in the first reaction step. Specifically, the outflow obtained in the first reaction step is separated into a third fraction and a fourth fraction in the separation step, and the obtained third fraction may be reused again in the first reaction step. In this case, HFO-1234yf is more efficiently produced, and the conversion of the starting material and the selectivity of the target product are further improved.

Further, as in the first fraction described above, the dehydrofluorination of HFC-245cb contained in the third fraction may be performed in the second reaction step.

EXAMPLES

The present invention is described in more detail below with reference to Examples. However, the present invention is not limited to the embodiments in the Examples.

Example 1

A dehydrofluorination reaction of the first reaction step was performed using HFC-245eb as a hydrofluorocarbon. As a catalyst, chromium oxide represented by the chemical formula: $CrO_{2.09}$ was used. The following pretreatment of catalyst was performed before the catalyst was used in the reaction. Specifically, anhydrous hydrogen fluoride diluted with nitrogen was passed through a reactor containing the catalyst, and the reactor was heated to 200 to 350° C. to perform a fluorination treatment.

The catalyst pretreated as above was placed in a reactor in which the dehydrofluorination reaction was to be performed, and under a nitrogen stream, the reactor was heated in an electric furnace. After the reactor reached a predetermined temperature (350° C. in this Example), HFC-245eb was introduced into the reactor, and the supply of nitrogen was stopped. Oxygen gas was appropriately introduced through the inlet of the reactor so that the amount of oxygen gas was 5 mol %, relative to the amount of HFC-245eb at the reactor inlet. Reaction operation conditions: pressure: 0.0 MPaG (G refers to a gage pressure); reaction temperature: 350° C.; and W/F0: 10 g·sec·ml$^{-1}$.

In this manner, the dehydrofluorination reaction of the first reaction step was performed, and the component composition of the outflow discharged from the reactor outlet was analyzed by gas chromatography. Table 1 below shows the results.

Comparative Example 1

The dehydrofluorination reaction of the first reaction step was performed using HFC-245eb as a hydrofluorocarbon. As a catalyst, a fluorinated alumina catalyst was used.

The catalyst was placed in a reactor in which the dehydrofluorination reaction was to be performed, and under a nitrogen stream, the reactor was heated in an electric furnace. After the reactor reached a predetermined temperature (350° C. in this Comparative Example), HFC-245eb was introduced into the reactor, and the supply of nitrogen was adjusted so that the concentration of HFC-245eb supplied was 40%. Oxygen gas was appropriately introduced through the inlet of the reactor so that the amount of oxygen gas was 5 mol %, relative to the amount of HFC-245eb at the reactor inlet. Reaction operation conditions: pressure: 0.0 MPaG; reaction temperature: 350° C.; and W/F0: 28 g·sec·ml$^{-1}$.

In this manner, the dehydrofluorination reaction of the first reaction step was performed, and the component composition of the outflow discharged from the reactor outlet was analyzed by gas chromatography. Table 1 below shows the results.

Comparative Example 2

The dehydrofluorination reaction of the first reaction step was performed using HFC-245eb as a hydrofluorocarbon. As a catalyst, a chromium oxyfluoride catalyst was used.

The catalyst was placed in a reactor in which the dehydrofluorination reaction was to be performed, and under a nitrogen stream, the reactor was heated in an electric furnace. After the reactor reached a predetermined temperature (420° C. in this Comparative Example), HFC-245eb was introduced into the reactor, and the supply of nitrogen was stopped. Oxygen gas was appropriately introduced through the inlet of the reactor so that the amount of oxygen gas was 5 mol %, relative to the amount of HFC-245eb at the reactor inlet. Reaction operation conditions: pressure: 0.0 MPaG; reaction temperature: 420° C.; and W/F0: 164 g·sec·ml$^{-1}$.

In this manner, the dehydrofluorination reaction of the first reaction step was performed, and the component composition of the outflow discharged from the reactor outlet was analyzed by gas chromatography. Table 1 below shows the results.

Comparative Example 3

The dehydrofluorination reaction of the first reaction step was performed as in Comparative Example 1, except that the reaction temperature was changed to 200° C. The component composition of the outflow discharged from the reactor outlet was analyzed by gas chromatography. Table 1 below shows the results.

Comparative Example 4

The dehydrofluorination reaction of the first reaction step was performed using HFC-245eb as a hydrofluorocarbon. As a catalyst, a catalyst in which 4.6 wt % of iron(III) chloride was supported on active carbon was used.

The catalyst was placed in a reactor in which the dehydrofluorination reaction was to be performed, and under a nitrogen stream, the reactor was heated in an electric furnace. After the reactor reached a predetermined temperature (250° C. in this Comparative Example), HFC-245eb was introduced into the reactor, and the supply of nitrogen was adjusted so that the concentration of HFC-245eb supplied was 50%. Oxygen gas was appropriately introduced through the inlet of the reactor so that the amount of oxygen gas was 5 mol %, relative to the amount of HFC-245eb at the reactor inlet. Reaction operation conditions: pressure: 0.0 MPaG; reaction temperature: 250° C.; and W/F0: 85 g·sec·ml$^{-1}$.

In this manner, the dehydrofluorination reaction of the first reaction step was performed, and the component composition of the outflow discharged from the reactor outlet was analyzed by gas chromatography. Table 1 below shows the results.

TABLE 1

| | Type of Catalyst | Reaction temperature (° C.) | 245 eb Conversion (%) | 1234 yf Selectivity (%) | 245 cb Selectivity (%) | 1234 ze (E/Z isomers) Selectivity (%) | 245 fa Selectivity (%) | $CO_2$ Selectivity (%) | Others Selectivity (%) |
|---|---|---|---|---|---|---|---|---|---|
| Example 1 | $CrO_{2.09}$ | 350 | 100 | 77.2 | 14.6 | 5.9 | 0.8 | 1.2 | 0.3 |
| Comp. Ex. 1 | Fluorinated alumina | 350 | 40 | 72 | — | 28 | — | — | — |
| Comp. Ex. 2 | Chromium oxyfluoride catalyst | 420 | 69 | 47 | — | — | — | — | — |
| Comp. Ex. 3 | Fluorinated alumina | 200 | 0 | 0 | — | — | — | — | — |
| Comp. Ex. 4 | Iron(III) chloride | 250 | 42 | 49 | — | — | — | — | — |

In Table 1, 245eb refers to 1,1,1,2,3-pentafluoropropane, 1234yf refers to 2,3,3,3-tetrafluoropropene, 245cb refers to 1,1,1,2,2-pentafluoropropane, 1234ze refers to 1,3,3,3-pentafluoropropene, and 245fa refers to 1,1,1,3,3-pentafluoropropane. The same applies to Tables 2 to 4.

Table 1 shows the type of catalyst used, the reaction temperature, and the selectivity for each component detected by gas chromatography (the conversion ratio for HFO-245eb).

In Example 1, the dehydrofluorination reaction was performed using chromium oxide represented by $CrO_m$ (m=2.09) as a catalyst; thus, the conversion of HFC-245eb used as the starting material was high, and HFO-1234yf, the target product, was produced with a high selectivity. In contrast, the conversion of HFC-245eb was low in all of the Comparative Examples, in which chromium oxide represented by $CrO_m$ (1.5<m<3) was not used. Moreover, in Comparative Example 1, in particular, 1234ze was produced in a large amount, relative to the amount of HFO-1234yf. In Comparative Example 2, although the contact time was set three times or more than that of the Example, and the reaction temperature was set higher than that of the Example, the conversion was not high, and the selectivity of HFO-1234yf was significantly low. Even if the contact time in Comparative Example 2 had been set as in Example 1, the conversion presumably would have been significantly low. In Comparative Example 3, the conversion was 0% since HFC-245eb used as the starting material did not react at all. In Comparative Example 4, the starting material conversion was only 42%, and the selectivity of HFO-1234yf was 49%, which was significantly lower than that of the Example. Although the contact time in Comparative Example 4 was longer than that of the Example, the conversion was low; even if the contact time had been set as in Example 1, the conversion presumably would have been even lower, compared to the Example.

Next, the effect of the reaction temperature was confirmed in the following Examples.

Example 2-1

A dehydrofluorination reaction of the first reaction step was performed using HFC-245eb as a hydrofluorocarbon. As a catalyst, chromium oxide represented by the chemical formula: $CrO_{2.09}$ was used. The following pretreatment of catalyst was performed before the catalyst was used in the reaction. Specifically, anhydrous hydrogen fluoride diluted with nitrogen was passed through a reactor containing the catalyst, and the reactor was heated to 200° C. to 380° C. to perform a fluorination treatment.

The pretreated catalyst was placed in a reactor in which the dehydrofluorination reaction was to be performed, and under a nitrogen stream, the reactor was heated in an electric furnace. After the reactor reached a predetermined temperature, HFC-245eb was introduced into the reactor, and the supply of nitrogen was stopped. Oxygen gas was appropriately introduced through the inlet of the reactor so that the amount of oxygen gas was 5 mol %, relative to the amount of HFC-245eb at the reactor inlet. Reaction operation conditions: pressure: 0.0 MPaG; reaction temperature: 200° C.; and W/F0: 32 g·sec·ml$^{-1}$.

In this manner, the dehydrofluorination reaction of the first reaction step was performed, and the component composition of the outflow discharged from the reactor outlet was analyzed by gas chromatography. Table 2 below shows the results.

Example 2-2

A dehydrofluorination reaction was performed as in Example 2-1, except that the reaction temperature was changed to 245° C. The component composition of the outflow discharged from the reactor outlet was analyzed by gas chromatography. Table 2 below shows the results.

Example 2-3

A dehydrofluorination reaction was performed as in Example 2-1, except that the reaction temperature was changed to 275° C. The component composition of the outflow discharged from the reactor outlet was analyzed by gas chromatography. Table 2 below shows the results.

Example 2-4

A dehydrofluorination reaction was performed as in Example 2-1, except that the reaction temperature was changed to 320° C. The component composition of the outflow discharged from the reactor outlet was analyzed by gas chromatography. Table 2 below shows the results.

Example 2-5

A dehydrofluorination reaction was performed as in Example 2-1, except that the reaction temperature was changed to 345° C. The component composition of the outflow discharged from the reactor outlet was analyzed by gas chromatography. Table 2 below shows the results.

Example 2-6

A dehydrofluorination reaction was performed as in Example 2-1, except that the reaction temperature was changed to 380° C. The component composition of the outflow discharged from the reactor outlet was analyzed by gas chromatography. Table 2 below shows the results.

TABLE 2

|  | Reaction temperature (° C.) | 245 eb Conversion (%) | 1234 yf Selectivity (%) | 245 cb Selectivity (%) | 1234 ze (E/Z) Selectivity (%) | 245 fa Selectivity (%) | $CO_2$ Selectivity (%) | Others Selectivity (%) |
|---|---|---|---|---|---|---|---|---|
| Example 2-1 | 200 | 14.1 | 93.3 | 3.0 | 1.2 | 2.3 | 0.0 | 0.2 |
| Example 2-2 | 245 | 58.9 | 90.7 | 5.2 | 1.3 | 2.7 | 0.0 | 0.1 |
| Example 2-3 | 275 | 92.0 | 86.4 | 9.0 | 2.2 | 2.3 | 0.0 | 0.1 |
| Example 2-4 | 320 | 100 | 75.3 | 18.7 | 4.3 | 1.3 | 0.3 | 0.1 |
| Example 2-5 | 345 | 100 | 77.2 | 14.7 | 5.8 | 0.8 | 1.2 | 0.3 |
| Example 2-6 | 380 | 100 | 81.5 | 7.5 | 7.9 | 0.6 | 2.0 | 0.5 |

Example 3-1

A dehydrofluorination reaction of the first reaction step was performed using HFC-245eb as a hydrofluorocarbon. As a catalyst, chromium oxide represented by the chemical formula: $CrO_{2.09}$ was used. The following pretreatment of catalyst was performed before the catalyst was used in the reaction. Specifically, anhydrous hydrogen fluoride diluted with nitrogen was passed through a reactor containing the catalyst, and the reactor was heated up to 380° C. to perform a fluorination treatment.

The catalyst pretreated as above was placed in a reactor in which the dehydrofluorination reaction was to be performed, and under a nitrogen stream, the reactor was heated in an electric furnace. After the reactor reached a predetermined temperature, HFC-245eb was introduced into the reactor, and the supply of nitrogen was stopped. Oxygen gas was appropriately introduced through the inlet of the reactor so that the amount of oxygen gas was 5 mol %, relative to the amount of HFC-245eb at the reactor inlet. Reaction operation conditions: pressure: 0.0 MPaG; reaction temperature: 200° C.; and W/F0: 5 g·sec·ml$^{-1}$.

In this manner, the dehydrofluorination reaction of the first reaction step was performed, and the component composition of the outflow discharged from the reactor outlet was analyzed by gas chromatography. Table 3 below shows the results.

Example 3-2

A dehydrofluorination reaction was performed as in Example 3-1, except that the reaction temperature was changed to 250° C. The component composition of the outflow discharged from the reactor outlet was analyzed by gas chromatography. Table 3 below shows the results.

Example 3-3

A dehydrofluorination reaction was performed as in Example 3-1, except that the reaction temperature was changed to 280° C. The component composition of the outflow discharged from the reactor outlet was analyzed by gas chromatography. Table 3 below shows the results.

Example 3-4

A dehydrofluorination reaction was performed as in Example 3-1, except that the reaction temperature was changed to 300° C. The component composition of the outflow discharged from the reactor outlet was analyzed by gas chromatography. Table 3 below shows the results.

Example 3-5

A dehydrofluorination reaction was performed as in Example 3-1, except that the reaction temperature was changed to 320° C. The component composition of the outflow discharged from the reactor outlet was analyzed by gas chromatography. Table 3 below shows the results.

TABLE 3

|  | Reaction temperature (° C.) | 245 eb Conversion (%) | 1234 yf Selectivity (%) | 245cb Selectivity (%) | 1234 ze (E/Z) Selectivity (%) | 245fa Selectivity (%) | $CO_2$ Selectivity (%) | Others Selectivity (%) |
|---|---|---|---|---|---|---|---|---|
| Example 3-1 | 200 | 6.8 | 95.1 | 1.7 | 1.8 | 1.4 | 0.0 | 0.0 |
| Example 3-2 | 250 | 37.3 | 93.2 | 3.0 | 1.9 | 1.9 | 0.0 | 0.0 |
| Example 3-3 | 280 | 68.6 | 90.8 | 4.8 | 2.8 | 1.7 | 0.0 | 0.0 |
| Example 3-4 | 300 | 85.4 | 89.5 | 5.4 | 3.8 | 1.2 | 0.1 | 0.0 |
| Example 3-5 | 320 | 90.8 | 89.6 | 4.8 | 4.5 | 1.0 | 0.1 | 0.0 |

As is clear from Table 3, the target product was produced with a high selectivity in a broad temperature range. Further, it is confirmed, in comparison with Comparative Example 3, that the conversion and selectivity improved even when the reaction was performed at 200° C. as in Examples 2-1 or 3-1.

Example 4-1

In accordance with the flow chart shown in FIG. 1, the outflow discharged after the dehydrofluorination reaction in Example 3-4 from the reactor outlet was subjected to a separation step, and the recovered HFC-245eb was reused. Specifically, the outflow F3 discharged from the outlet of the reactor in which the dehydrofluorination reaction of Example 3-4 was performed was supplied to an apparatus in which the separation step was to be performed, and the separation step was performed. As a result of this separation step, a first fraction having a greater concentration of HFC-245eb than before the separation step, and a second fraction having a lower concentration of HFC-245eb than before the separation step were obtained. The first fraction F4 was reused in the dehydrofluorination reaction to perform a dehydrofluorination reaction of HFC-245eb contained in the first fraction. The target HFO-1234yf (F5) was separated and recovered after the separation step comprising rectification, extractive distillation, or the like.

Table 4 shows the flow rate of each component of F1 to F6 shown in FIG. 1.

TABLE 4

| | Flow rate (mol/min) | | | | | |
|---|---|---|---|---|---|---|
| Component | F1 | F2 | F3 | F4 | F5 | F6 |
| 245 eb | 0.72 | 0.84 | 0.12 | 0.12 | 0 | 0 |
| 1234 yf | 0 | 0 | 0.64 | 0 | 1.14 | 0 |
| 245 cb | 0 | 0 | 0.04 | 0 | 0.04 | 0 |
| 1234 ze(E/Z) | 0 | 0 | 0.027 | 0 | 0.027 | 0 |
| 245 fa | 0 | 0 | 0.009 | 0 | 0.009 | 0 |
| Others | 0 | 0 | 0.004 | 0 | 0 | 0.004 |
| HF | 0 | 0 | 0.667 | 0 | 0 | 0.667 |
| $O_2$ | 0.042 | 0.042 | 0 | 0 | 0.042 | 0 |

The invention claimed is:
1. A method for producing a fluorine-containing olefin, the method comprising a first reaction step comprising subjecting a hydrofluorocarbon to dehydrofluorination in the presence of a catalyst, wherein:
the hydrofluorocarbon is HFC-245eb,
the catalyst comprises a chromium oxide represented by the chemical formula: $CrO_m$, wherein $2.05 \leq m \leq 2.3$, and
the dehydrofluorination in the first reaction step is performed at 200 to 380° C.

2. The method for producing a fluorine-containing olefin according to claim 1,
wherein a total S1 (mol/min) is 20% or less, relative to a flow rate S (mol/min), the flow rate S being a flow rate of an entire reaction product discharged after the first reaction step from a reactor in which the first reaction step is performed, the total S1 being a flow rate of E- and Z-isomers of HFO-1234ze and a flow rate of HFC-245fa contained in the entire reaction product.

3. The method for producing a fluorine-containing olefin according to claim 2, wherein the total S1 (mol/min) is 10% or less, relative to the flow rate S (mol/min).

4. The method for producing a fluorine-containing olefin according to claim 2, wherein the total S1 (mol/min) is 5% or less, relative to the flow rate S (mol/min).

5. The method for producing a fluorine-containing olefin according to claim 1,
the method comprising a separation step after the first reaction step, the separation step comprising separating a portion of or all of the outflow obtained from the reactor in which the first reaction step is performed into at least a first fraction and a second fraction,
wherein the first fraction has a greater concentration of HFC-245eb than before the separation step, and the second fraction has a lower concentration of HFC-245eb than before the separation step, and
wherein at least a portion of the first fraction is subjected to dehydrofluorination after the separation step.

6. The method for producing a fluorine-containing olefin according to claim 5, wherein at least a portion of the first fraction is reused in the first reaction step of dehydrofluorination.

7. The method for producing a fluorine-containing olefin according to claim 1, wherein the hydrofluorocarbon is subjected in combination with oxygen gas to the first reaction step.

8. The method according to claim 7, wherein a flow rate (mol/min) of the oxygen gas is 0.1% or more and 10% or less, relative to a flow rate (mol/min) of the hydrofluorocarbon.

9. The method for producing a fluorine-containing olefin according to claim 1, wherein the chromium oxide further contains a Group 5 metal.

10. The method for producing a fluorine-containing olefin according to claim 9, wherein the number of atoms of the Group 5 metal contained in the chromium oxide is 0.1% or more and 50% or less, relative to the total number of atoms of the metal contained in the chromium oxide.

* * * * *